US006821730B2

(12) United States Patent
Hannah

(10) Patent No.: US 6,821,730 B2
(45) Date of Patent: Nov. 23, 2004

(54) CARBON NANOTUBE MOLECULAR LABELS

(75) Inventor: Eric C. Hannah, Pebble Beach, CA (US)

(73) Assignee: Intel Corporation, Santa Clara, CA (US)

( * ) Notice: Subject to any disclaimer, the term of this patent is extended or adjusted under 35 U.S.C. 154(b) by 0 days.

(21) Appl. No.: 09/991,610

(22) Filed: Nov. 9, 2001

(65) Prior Publication Data

US 2004/0110128 A1 Jun. 10, 2004

(51) Int. Cl.$^7$ .......................... C12Q 1/68; C12N 11/08; G01N 33/544
(52) U.S. Cl. .............................. 435/6; 435/4; 435/180; 435/287.1; 435/287.2; 436/518; 436/528
(58) Field of Search ........................... 435/3, 4, 6, 7.1, 435/7.92, 174, 180, 287.1, 287.2; 436/518, 528, 524, 536

(56) References Cited

U.S. PATENT DOCUMENTS

| | | | |
|---|---|---|---|
| 5,202,231 A | | 4/1993 | Drmanac et al. |
| 5,332,666 A | | 7/1994 | Prober et al. |
| 5,436,130 A | | 7/1995 | Mathies et al. |
| 5,780,232 A | | 7/1998 | Arlinghaus et al. |
| 5,821,058 A | | 10/1998 | Smith et al. |
| 5,821,060 A | | 10/1998 | Arlinghaus et al. |
| 5,866,434 A | * | 2/1999 | Massey et al. ............... 436/526 |
| 5,972,619 A | | 10/1999 | Drmanac et al. |
| 6,045,996 A | | 4/2000 | Cronin et al. |
| 6,083,695 A | | 7/2000 | Hardin et al. |
| 6,140,045 A | * | 10/2000 | Wohlstadter et al. .......... 435/6 |
| 6,187,823 B1 | | 2/2001 | Haddon et al. |
| 6,258,401 B1 | | 7/2001 | Crowley |
| 6,283,812 B1 | | 9/2001 | Jin et al. |
| 6,297,592 B1 | | 10/2001 | Goren et al. |
| 6,303,094 B1 | | 10/2001 | Kusunoki et al. |

OTHER PUBLICATIONS

Adams, Thomas A. II, "Physical Properties of Carbon Nanotubes,"[on line], [Retrieved on Oct. 22, 2001]. Retrieved from the Internet URL:<http://www.pa.msu.edu./cmp/csc/ntproperties/main.html.
Arepalli, S., et al., "Electronically excited $C_2$ from laser photodissociated $C_{60}$," Chemical Physics Letters, 320 (2000), pp. 26–34.
Bonard, Jean–Marc, et al., "Why are carbon nanotubes such excellent field emitters?" [Retrieved on Oct. 22, 2001]. Retrieved from the Internet URL:<http://www.foresight.org/Conferences/MNT6/Papers/Chatelain. pp. 1–10.

Han, H.X., et al., "Photoluminescence Study of Carbon Nanotubes" Los Alamos Physics Preprints: cond–mat/0004035, Apr. 4, 2000, pp. 1–6.
Hertel, Tobias, et al., "Electron–Photon Interaction in Single–Wall Carbon Nanotubes: A Time–Domain Study," Physical Review Letters, 2000, 84: 5002–5005.
Mason, Jack, "Nanotubes Fall Into Line," [on line], [Retrieved on Oct. 23, 2001]. Retrieved from the Internet, Technology Review, May 24, 2001, pp. 1–2.
Odom, Teri, et al. "Atomic structure and electronic properties of single–walled carbon nanotubes" Nature, 1998, 391: 62–64.
Parker, Deborah et al. "High–Yield synthesis, separation, and mass–spectrometric characterization of fullerenes $C_{60}$ to $C_{266}$ " J. Am. Chem. Soc., 1991, 113: 7499–7503.
Rinzler, Andrew, et al. "Session S20–Nanotubes VII: Spectroscopy and Optical Properties," Focus Session, Wednesday afternoon, Mar. 14, Room 401, Washington State Convention Center. [Retrieved on Oct. 23, 2001]. Retrieved fron the Internet URL:<http://www.aps.org/meet/MAR01/baps/abs/S6800.html. pp. 1–5.
Rochefort, Alain, "The Effects of Finite Length on the Electronic Structure of Carbon Nanotubes" Los Alamos Physics Preprints:cond–mat/9808271, Aug. 24, 1998, pp. 1–8.
Sasaki, K. "Vacuum structure of Carbon Nanotube Torus" Los Alamos Physics Preprints:cond–mat/0106190, Jun. 11, 2001, pp. 1–10.
Venema, Liesbeth, et al., Imaging Electron Wave Functions od Quantized Energy Levels in Carbon Nanotubes, Los Alamos Physics Preprints:cond–mat/9811317, Nov. 23, 1998, pp. 1–14.
Wildoer, Jeroen et al., "Electronic structure of atomically resolved carbon nanotubes" Nature, 1998, 391: 59–62.

* cited by examiner

Primary Examiner—Padmashri Ponnaluri
Assistant Examiner—My-Chau T. Tran
(74) Attorney, Agent, or Firm—Blakely, Sokoloff, Taylor & Zafman LLP

(57) ABSTRACT

The methods and compositions disclosed herein concern highly diverse, novel labels comprising carbon nanotubes of discrete lengths and/or diameters. In certain embodiments, the nanotube labels may be attached to oligonucleotide or similar probes for use in DNA sequencing. Upon excitation, for example by an electron beam or UV laser, the carbon nanotubes exhibit distinguishable emission spectra. The nanotube labels are not limited to DNA sequencing, but rather are of use in any application where large numbers of distinguishable labels are desirable. Novel methods for production of carbon nanotubes and apparatus for detection of nanotubes are also disclosed herein.

22 Claims, 4 Drawing Sheets

CARBON NANOTUBE MOLECULAR LABELS

BACKGROUND OF THE INVENTION

1. Field of the Invention

The present invention relates to the fields of carbon nanotube technology and molecular biology. In particular, the invention relates to methods and composition for producing large numbers of distinguishable labels comprising carbon nanotubes. More particularly, the invention relates to compositions, apparatus and methods of use of carbon nanotube labels for DNA (deoxyribonucleic acid) sequencing and other applications.

2. Background

Carbon nanotubes may be thought of as sheets of graphite that have been rolled up into cylindrical tubes. The basic repeating unit of the graphite sheet consists of hexagonal rings of carbon atoms, with a carbon-carbon bond length of about 1.42 Å. Depending on how they are made, the tubes may multiple walled or single walled. A typical single walled carbon nanotube (SWNT) has a diameter of about 1.2 to 1.4 nm.

The structural characteristics of nanotubes provide them with unique physical properties. Nanotubes may have up to 100 times the mechanical strength of steel and can be up to 2 mm in length. They exhibit the electrical characteristics of either metals or semiconductors, depending on the degree of chirality or twist of the nanotube. Different chiral forms of nanotubes are known as armchair, zigzag and chiral nanotubes. Carbon nanotubes have been used as electrical conductors and as electron field emitters. The electronic properties of carbon nanotubes are determined in part by the diameter and length of the tube.

Many existing methods of use in molecular biology would benefit from the availability of a highly diverse set of tag molecules that could be used as molecular labels to detect binding of specific analytes to various ligands. For example, the speed and efficiency of nucleic acid sequencing would be greatly enhanced by the availability of unique labels capable of identifying all possible nucleic acid sequences for oligonucleotides of five, six, seven, eight or even more nucleotide residues in length. At present, no such set of distinguishable labels with the required degree of diversity exists.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Definitions

Figure 1:
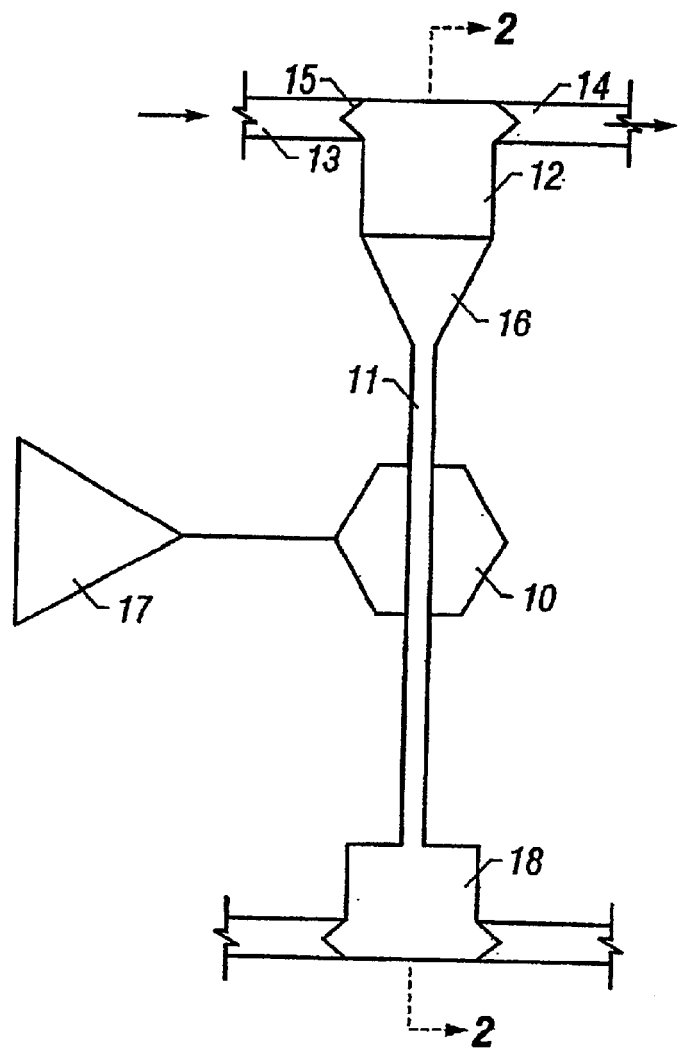
FIG. 1 illustrates an embodiment of a microfluidic device.

As used herein, "a" or "an" may mean one or more than one of an item.

As used herein, the term "about" when applied to a number means within plus or minus three percent of that number. For example, "about 100" means any integer between 97 and 103.

"Nucleic acid" encompasses DNA, RNA (ribonucleic acid), single-stranded, double-stranded or triple stranded and any chemical modifications thereof, although single-stranded nucleic acids are preferred. Virtually any modification of the nucleic acid is contemplated by this invention. Within the practice of the present invention, a "nucleic acid" may be of almost any length, from 10, 20, 50, 100, 200, 300, 500, 750, 1000, 1500, 2000, 2500, 3000, 3500, 4000, 4500, 5000, 6000, 7000, 8000, 9000, 10,000, 15,000, 20,000, 30,000, 40,000, 50,000, 75,000, 100,000, 150,000, 200,000, 500,000, 1,000,000, 2,000,000, 5,000,000 or even more bases in length, up to a full-length chromosomal DNA molecule.

As used herein the terms "tag" and "label" are used interchangeably to refer to any atom, molecule, compound or composition that can be used to identify an analyte to which the label is attached. In various embodiments, such attachment may be either covalent or non-covalent. In certain embodiments, the labels have physical characteristics that facilitate the identification of the label. In non-limiting examples, labels may be fluorescent, phosphorescent, luminescent, electroluminescent, chemiluminescent or may exhibit detectable Raman or other spectroscopic characteristics. It is anticipated that virtually any technique capable of detecting and identifying a labeled species may be used, including visible light, ultraviolet and infrared spectroscopy, Raman spectroscopy, nuclear magnetic resonance, positron emission tomography and other methods known in the art.

"Analyte" means any compound or aggregate of interest to detect and/or label. Non-limiting examples of analytes include a protein, peptide, carbohydrate, polysaccharide, glycoprotein, nucleic acid, lipid, hormone, receptor, antigen, allergen, antibody, substrate, metabolite, cofactor, inhibitor, drug, pharmaceutical, nutrient, toxin, poison, explosive, pesticide, chemical warfare agent, biohazardous agent, prion, vitamin, heterocyclic aromatic compound, carcinogen, mutagen, narcotic, amphetamine, barbiturate, hallucinogen, waste product, contaminant or other molecule. "Analytes" are not limited to single molecules, but may also comprise complex aggregates of molecules, such as a virus, bacterium, spore, mold, yeast, algae, amoebae, Ghiardia, unicellular organism, pathogen, cell or infectious agent.

Carbon Nanotubes

Optical Properties of Nanotubes vs. Tube Length

Certain embodiments concern compositions comprising carbon nanotubes of discrete diameters and lengths. Such compositions are of use as molecular labels. When the nanotubes are excited with, for example, a UV (ultraviolet) laser or fast electron beam, electrons are excited into high energy states. The electrons rapidly return to the ground state by means of photon emission. The frequency of the emitted photons is a function of tube length and diameter. Carbon nanotubes provide a novel type of molecular label with a very high number of distinguishable tags, associated with nanotubes of different length and diameter.

Carbon nanotubes have strong electronic properties that are modulated by the length and diameter of the tube. This results from the one-dimensional form of the tube, which is an almost textbook example of a quantum mechanical system. The sensitivity of the electronic wavefunction to length is illustrated by a simple estimate for the energy level splitting of a tube of length L.

$$\Delta E = h v_F / 2L$$

Where h is Planck's constant and vF is the Fermi velocity ($8.1 \times 10^5$ m/sec) (Venema et al., "Imaging Electron Wave Functions of Carbon Nanotubes," Los Alamos Physics Preprints:cond-mat/9811317, 23 Nov. 1996.) For a nanotube of 30 nm in length, the value of the simple estimate for the energy level splitting is 0.06 eV (Venema et al., 1996). The difference between electron energy levels is inversely proportional to the length of the nanotube, with finer splitting observed for longer tubes.

For certain embodiments, nanotubes to be used as labels may have tube lengths of about 10 to 100 nm. Nanotube stability may be decreased at lengths of less than about 10 nm and in other embodiments, a nanotube length varying between approximately 20 to 200 nm may be used to provide optical signals in the ultraviolet, visible and infrared ranges, although detectors capable of identifying signals at greater or lower wavelengths may be used. In alternative embodiments, nanotube lengths of 15 to 400 nm or even 5 to 800 nm are contemplated, with micron length nanotubes of use in certain applications. The length or diameter of the nanotubes to be used as labels is not limited and nanotubes of virtually any length or diameter are contemplated. Nor is there a limitation as to the type of detector used. In alternative embodiments, detectors that are capable of analyzing emitted electromagnetic radiation in the ultraviolet, visible, infrared, Raman, microwave or even radiofrequency ranges of the spectrum are contemplated. In certain embodiments, nanotube labels with emission spectra in the visible light range may be preferred.

The optical properties of carbon nanotubes are also a function of tube diameter. In certain embodiments, single walled carbon nanotubes with a diameter of about 1.2 to 1.4 nm may be used. The relationship between fundamental energy gap (highest occupied molecular orbital—lowest unoccupied molecular orbital) and tube diameter may be modeled by the following function.

$$E_{gap} = 2 y_0 a_{cc} / d$$

Where $y_0$ is the carbon-carbon tight bonding overlap energy (2.7±0.1 eV), $a_{cc}$ is the nearest neighbor carbon-carbon distance (0.142 nm) and d is the tube diameter (Jeroen et al, *Nature* 391:59–62, 1998). The relationship predicts a fundamental gap in the range from around 0.4 eV to 0.7 eV (Jeroen et al., 1998). A small gap has also been predicted to exist at the Fermi energy level (highest occupied energy level) in metallic nanotubes (Odom et al., *Nature* 391:62–64, 1998). As energy is increased over the Fermi energy level, sharp peaks in the density of states, referred to as Van Hove singularities, appear at specific energy levels (Odom et al., 1998). The predicted optical spectrum of carbon nanotubes is given by the following relationship.

$$\Delta E = h \times \Omega$$

Where $\Delta E$ is the energy difference between occupied and unoccupied molecular orbitals, h is Planck's constant divided by 2 Pi and $\Omega$ is the angular wavefunction frequency. The optical emission spectrum of carbon nanotubes is dominated by the transitions between Van Hove singularities.

The photoluminescence characteristics of metallic carbon nanotubes have been examined (Han et al., "Photoluminescence Study of Carbon Nanotubes," Los Alamos Physics Preprints: cond-mat/004035, Apr. 4, 2000.) Optical transitions between the σ and π peaks are allowed, predicting light emission at approximately 2 eV, about in visible range of the spectrum. A strong visible light emission has been observed from carbon nanotubes excited by UV lasers (Han et al., 2000). The light bands emitted from a large number of nanotubes in an exposed sample area were centered in the range from 2.05 to 2.3 eV for different samples, which is far beyond the fundamental gaps of semiconducting carbon nanotubes. Light intensities also showed a super-linear dependence upon the excitation intensity, which is not consistent with a single photon excitation process (Han et al., 2000). Based on the theoretical analysis of electronic band structures, especially on the symmetry properties of both σ and π electronic states, a two-step transition mechanism has been suggested for excitation and photon emission (Han et al, 2000).

Spectroscopy and topography line scans along the length of a 1.4 nm diameter by 30 nm long carbon nanotube showed electron wave functions of discrete electron states, as well as the atomic lattice (Venema et al., 1998). Changes as small as 60 meV strongly changed the position of the electron wavefunctions, providing clear evidence of a finite length effect on nanotube electronic properties.

The electronic structure of finite-length armchair carbon nanotubes was investigated using ab-initio and semi-empirical quantum chemistry techniques (Rochefort et al., "The Effects of Finite Length on the Electronic Structure of Carbon Nanotubes," Los Alamos Physics Preprints: cond-mat/9808271, Aug. 24, 1998.) Armchair tubes that were metallic when infinitely long developed a band-gap at finite lengths, with the value of the band-gap decreasing with increasing tube length (Rochefort et al., 1998). The decrease in band-gap showed an oscillation in short tubes that was ascribed to changes in the HOMO (highest occupied molecular orbital) and LUMO (lowest unoccupied molecular orbital) orbitals of the tubes as a function of increasing length (Rochefort et al., 1998). The DOS (density of states) spectrum of short nanotubes evolved with increasing length from a zero-dimensional (0-D) system to a delocalized one-dimensional (1-D) system, with transition complete by a 10 nm tube length (Rochefort et al., 1998). This theoretical analysis further substantiates the effect of nanotube length on the electron wavefunction.

The characteristic electronic wavefunction of carbon nanotubes provides a series of peaks on the optical emission spectra of excited carbon nanotubes. The number and location of those peaks within the emission spectrum are affected by the length and diameter of the nanotube. Each nanotube of discrete length and diameter may be identified by the pattern of optical emission peaks detected in response to excitation.

Production of Carbon Nanotube Labels

A variety of methods are available for production and use of carbon nanotube labels. These fall into three general categories, discussed below. Although certain embodiments provide for synthesis of carbon nanotubes of desired length and diameter, it is also contemplated that nanotubes may be obtained from commercial sources, for example, CarboLex (Lexington, Ky.), NanoLab (Watertown, Mass.), Materials and Electrochemical Research (Tucson, Ariz.) or Carbon Nano Technologies Inc. (Houston, Tex.). Depending on the application, some processing of either synthesized or obtained nanotubes may be appropriate before use. Processing may include purification of nanotubes from other contaminants, separation of nanotubes of mixed diameter and/or length into nanotubes of discrete diameter and length, removal of nanotube end caps and/or covalent modification to facilitate attachment of the nanotube to an analyte or probe.

In certain embodiments, carbon nanotubes of varying length and/or diameter may be produced by a variety of techniques known in the art, including but not limited to carbon-arc discharge, chemical vapor deposition via catalytic pyrolysis of hydrocarbons, plasma assisted chemical vapor deposition, laser ablation of a catalytic metal-containing graphite target, or condensed-phase electrolysis. (See, e.g., U.S. Pat. Nos. 6,258,401, 6,283,812 and 6,297,592.) Compositions comprising mixtures of different length carbon nanotubes may be separated into discrete size classes according to nanotube length and diameter, using any method known in the art. In some embodiments, nanotubes may be size sorted by mass spectrometry (See, Parker et al., "High yield synthesis, separation and mass spectrometric characterization of fullerene C60–C266," J. Am. Chem. Soc. 113:7499–7503, 1991). Alternatively, nanotubes may be sorted using an AFM (atomic force microscope) or STM (scanning tunneling microscope) to precisely measure the geometry of individual nanotubes before attaching them to appropriate analytes or probes. Other methods of size fractionation known in the art, such as gas chromatography, time of flight mass spectrometry, ultrafiltration or equivalent techniques are contemplated. Once sorted, the carbon nanotubes may be derivatized as discussed below and covalently attached to oligonucleotide probes of known sequence.

In alternative embodiments, compositions comprising carbon nanotubes of varying tube length and/or diameter may be synthesized by standard techniques as discussed above. The mixture of nanotubes may be derivatized and attached to oligonucleotide probes of random nucleic acid sequence. The labeled oligonucleotide probes may be separated by, for example, binding to a nucleic acid chip (e.g., U.S. Pat. Nos. 5,861,242 and 5,578,832). In certain embodiments, the chip may be designed to contain one molecule of each oligonucleotide sequence to be labeled. Hybridization may be allowed to occur until the chip is saturated, that is, a single labeled oligonucleotide probe is bound to each position on the chip. The optical signal from each labeled hybridized probe molecule may be detected, identifying the carbon nanotube attached to that probe nucleic acid sequence. In certain embodiments, DNA chips containing all possible hybridizing sequences for probes of 5 (1,024 sequences), 6 (4,096 sequences) or more nucleotides in length may be used, providing a complete set of nanotube labeled probes.

The minimum incremental change in tube length possible for a carbon nanotube is the length of the carbon-carbon bond, or about 0.142 nm. With a range of tube lengths of 200 nm, this would allow for about 1400 discrete molecular labels. However, the labeling method is not limited to a single nanotube per analyte or probe. In alternative embodiments, multiple nanotubes of different length and diameter may be attached to a single analyte or probe. Using combinations of nanotubes of different length, the number of possible distinguishable labels increases exponentially. In preferred embodiments, a single nanotube is attached to a single analyte or probe for simplicity of analysis.

Other embodiments comprise methods of producing carbon nanotubes of defined length and diameter. In a non-limiting exemplary embodiment, a chip may contain a layer of SiC of preselected thickness, overlaying a layer composed, for example, of silicon or silicon doped with catalysts (e.g. metal atoms such as nickel). Using standard chip processing methods, such as photolithography and etching or laser ablation, the SiC layer may be divided into SiC deposits of any desired length, width, thickness and shape. Subsequently the chip may be heated under a vacuum, for example at about $10^{-7}$ Torr at about 1400° C., or alternatively from about $10^{-3}$ to $10^{-12}$ Torr, $10^{-4}$ to $10^{-10}$ Torr, or $10^{-5}$ to $10^{-9}$ Torr, and from 1200 to 2200° C. 1400 to 2000° C. Under these conditions, SiC crystals spontaneously decompose and lose silicon atoms (U.S. Pat. No. 6,303,094). The remaining carbon atoms spontaneously assemble into carbon nanotubes. The size and shape of the SiC deposits may be precisely controlled to produce carbon nanotubes of any desired length and diameter. Since the nanotubes formed may cannibalize each other at higher temperatures, the temperature must be controlled to prevent that from occurring. A given chip surface could be etched to produce a class of nanotubes of almost identical diameter and length, or to produce groups of nanotubes of multiple desired lengths and diameters. Once the nanotubes have been formed, they may be collected, derivatized and attached to analytes or probes.

The exemplary embodiments discussed above are not limiting and any method of producing carbon nanotubes of desired length and diameter may be used (e.g., U.S. Pat. Nos. 6,258,401; 6,283,812 and 6,297,592). Alternative methods for nanotube production include, but are not limited to, growing nanotubes of a desired diameter inside the pores of a block copolymer or a zeolite, or embedding them in a matrix, and adjusting the length by trimming with a reactive ion etch coupled with a masking step. Alternatively, nanotube length could be adjusted by using a laser beam, electron beam, ion beam or gas plasma beam to trim the ends. A light vacuum suction or gas blow could be used to remove truncated ends of nanotubes. Alternatively, the ends of the nanotubes could be brought into contact with a hot blade in an oxygen-containing atmosphere to oxidatively remove the ends of the tubes. A block containing the nanotubes could also be sectioned or polished to truncate the nanotubes. Following truncation, the copolymer, zeolite or other matrix may be removed, for example, by etching or dissolution in an appropriate solvent.

Carbon Nanotube Derivitization

In certain embodiments, carbon nanotubes may be derivatized with reactive groups to facilitate attachment to analytes or probes. In preferred embodiments, each nanotube may be derivatized to contain a single reactive group at one end of the tube, although it is contemplated that nanotubes may contain more than one reactive group located anywhere on the tube. In a non-limiting example, nanotubes may be derivatized to contain carboxylic acid groups (U.S. Pat. No. 6,187,823). Carboxylate derivatized nanotubes may be attached to nucleic acid probes or other analytes by standard chemistries, for example by carbodiimide mediated formation of an amide linkage with a primary or secondary amine group located on a probe or analyte. The methods of derivatization and cross-linking are not limiting and any reactive group or cross-linking methods known in the art may be used.

The nanotube compositions and methods disclosed above may be of use to provide distinguishable molecular labels for a variety of analytes or probes. In certain embodiments, the nanotubes may be attached to nucleic acid probes of known sequence. Such labeled probes could be used, for example, in nucleic acid hybridization experiments to detect the presence of one or more specific complementary nucleic acid sequences in a sample. Present methods of such detection may rely on hybridization to DNA chips, containing probes of known sequence attached to specific location on the chip. Binding of a nucleic acid to that chip site indicates the presence of the complementary sequence. However, such chips are presently designed for detection of known gene or cDNA (complementary DNA) sequences and are not well suited to detecting and identifying completely unknown nucleic acid sequences. Since the labeled probes disclosed herein can provide a complete, distinguishable set of all possible nucleic acid sequences of a given length, it is possible to hybridize unknown samples to such probe sets and identify all complementary sequences contained in the sample. Alternative embodiments are directed to nucleic acid sequencing, discussed below. However, the nanotube labels disclosed herein are not limited to the exemplified embodiments, but may be used for any application in which a highly diverse set of distinguishable labels would be of use.

Nucleic Acid Sequencing

In certain embodiments a small quantity of a nucleic acid to be sequenced may be hybridized with a probe library or a plurality of probe libraries. Probe libraries can be a group of oligonucleotides or oligonucleotide analogs. In preferred embodiments, each probe in a library is uniquely and detectably labeled with one or more carbon nanotubes. By identifying the probes hybridized to a nucleic acid, the linear order of probes can be analyzed and a nucleic acid sequence determined. In certain embodiments, analysis of a nucleic acid molecule(s) hybridized to a series of probes can entail monitoring the nucleic acid using a detection unit operatively connected to a microfluidic apparatus. In particular embodiments one or more microfluidic chambers, channels, capillaries, pores, valves or combinations thereof may be used to process, move, and/or position a nucleic acid for analysis. A microfluidic device may be designed to position a nucleic acid molecule(s) in an extended conformation for analysis. In certain embodiments, the nucleic acid may be manipulated so that only a single nucleic acid molecule moves along a microchannel at a time.

FIG. 1 illustrates an exemplary embodiment of an apparatus that may be used in the practice of certain methods of the invention. A detection unit 10 may be positioned to monitor nucleic acid molecules flowing through a channel 11. The apparatus will typically include an input or reaction chamber 12 where one or more nucleic acids may be hybridized to a probe library. An input chamber 12 may have an inlet port 13 and an outlet port 14 to provide for the flow of reagents. Flow in and out of input chamber 12 can be controlled by microvalves 15 and the like operatively connected to the inlet port 13 and outlet port 14.

A focusing region 16 may be used to hydrodynamically focus fluids containing hybridized nucleic acid(s). Hydrodynamic focusing may separate one or more nucleic acid molecules as fluid flows from an input chamber 12 to a channel 11. As a nucleic acid molecule moves through a focusing region 16 it is extended to an approximate linear conformation.

A channel 11 may be positioned to flow fluid or solutions by a detection unit 10. A detection unit 10 will typically detect the spectral signature of each labeled probe, preferably in sequential order. A detection unit 10 may be operatively connected to a data processing system 17 for storage and analysis of detected spectra.

The channel 11 will have a lumen or groove that is in fluid communication with a fluid focusing region and an output chamber 18. An output chamber 18 may be used for collecting or sorting fluids flowing out of channel 11. An output chamber 18 may also be operatively connected to means for producing a motive force for fluid flow. Means for producing a motive force include but are not limited to thermal, electroosmotic, pressure, and/or vacuum gradients.

Figure 2:
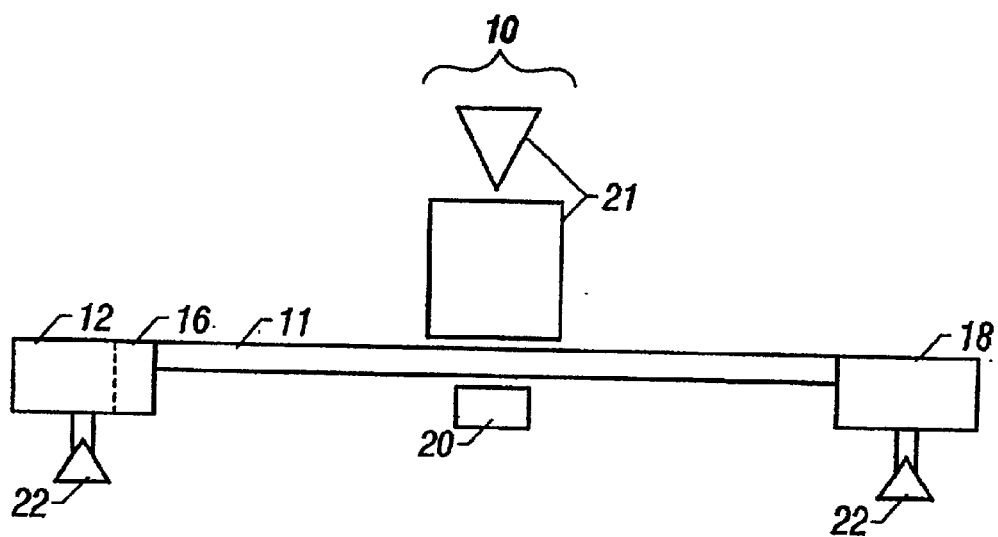
FIG. 2 illustrates a cross-sectional view along the line 2—2 in FIG. 1.

FIG. 2 illustrates a cross-sectional view of the apparatus of FIG. 1 along the line 2—2. The illustration in FIG. 2 shows an input chamber 12 in fluid communication with a channel 11. The channel 11 is in fluid communication with an output chamber 18. The channel 11 may be positioned adjacent to a detector 20 that is part of the detection unit 10. Included in the detection unit 10 can be an excitation source 21, preferably a micro electron beam column. In certain embodiments the detector may be operatively connected to a data processing system. Also illustrated in the cross-sectional view are fluid control means 22. The fluid control means 22 may be sources of pressure, vacuum, heat, cooling, electric potential or other gradients to control the flow of fluids within the apparatus. The excitation source 21 may be positioned to provide excitation energy to labeled probes as they flow in the channel 11. Energy from the excitation source 21 may be absorbed by a labeled probe molecule and portions of that energy may be emitted from the label as a detectable signal, preferably a label specific spectral signal.

Figure 3:
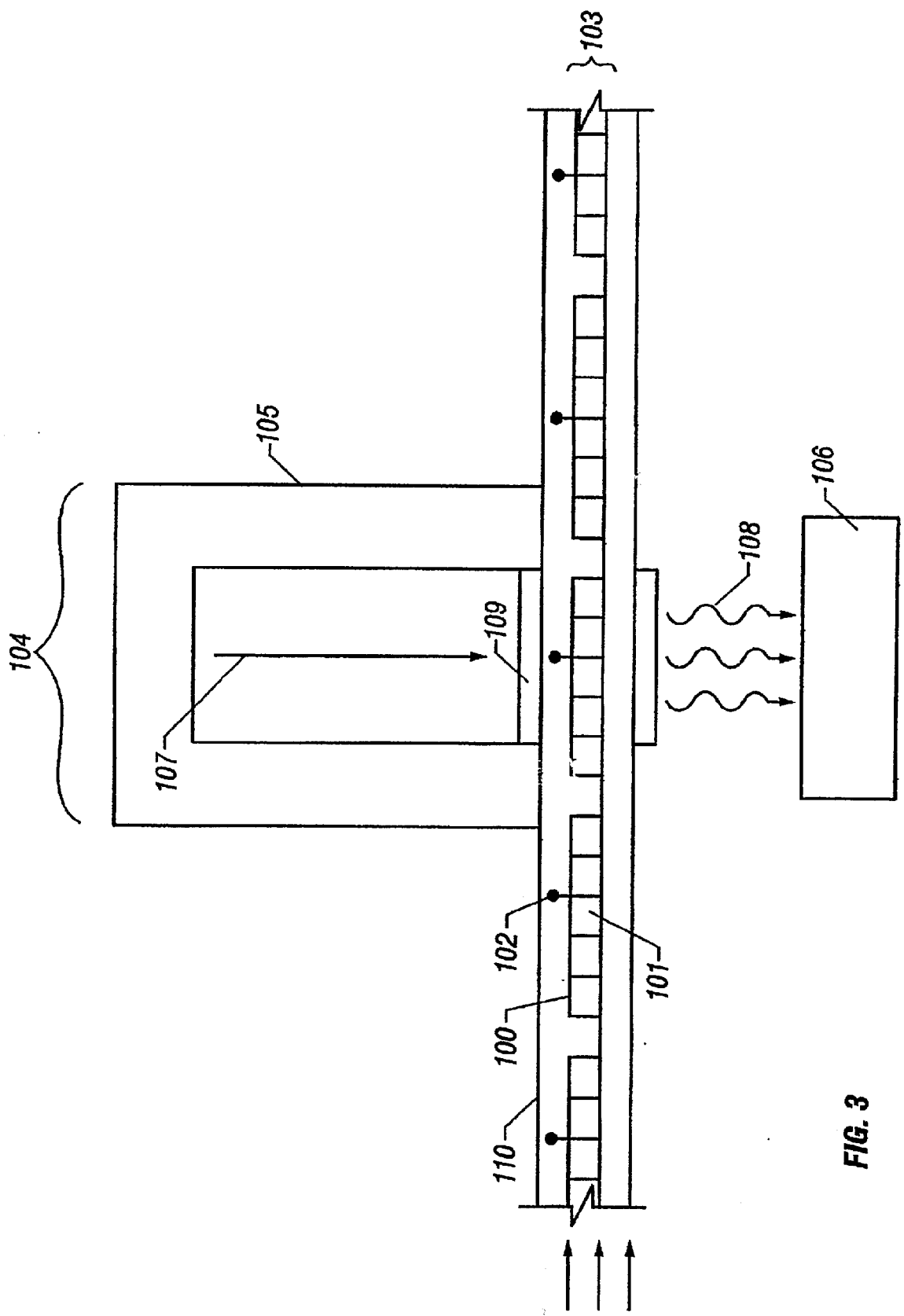
FIG. 3 illustrates an embodiment of a detection unit.

FIG. 3 illustrates an expanded view of a signal-monitoring portion of an exemplary apparatus. In one embodiment, one or more labeled probes 100 are associated with the nucleic acid molecule(s) 101 in a sequence specific manner, for example by Watson-Crick base pairing, forming a double-stranded hybridized nucleic acid 103. A probe may be detected as it moves past detection unit 104. In preferred embodiments, individual probes 100 are detected in sequential order as they move past detection unit 104 in a linear sequence, corresponding to the linear sequence of the nucleic acid 101.

Detection unit 104 is generally comprised of an excitation source 105 and a detector 106. In one embodiment the excitation source 105 comprises a micro electron beam device (micro e-beam) 107. The micro e-beam 107 may be focused to pass through a window 109 in the channel 110 and within an appropriate distance of a probe 100 in order to excite the probe 100 and transfer energy to a label 102 attached to the probe 100 by coulombic induction. An excited label 102 subsequently emits a signal 108 that is monitored by a detector 106. Preferably the signal 108 is an emission spectrum unique to the particular label 102. In certain embodiments, the time of each probe 100 passing a detector 106 is determined and recorded. Thus, if a hybridized nucleic acid 103 is passing a detector 106 at a constant speed (nucleotide per time unit), gaps in a probe hybridization pattern can be detected. Such gaps may occur where hybridization between the nucleic acid 101 and the library of probes 100 is incomplete. Hybridization gaps can be addressed by using multiple hybridizations with multiple pools of probes 100 or by analyzing a plurality of nucleic acid molecules 103 that have been hybridized to one or more probe libraries.

Figure 4:
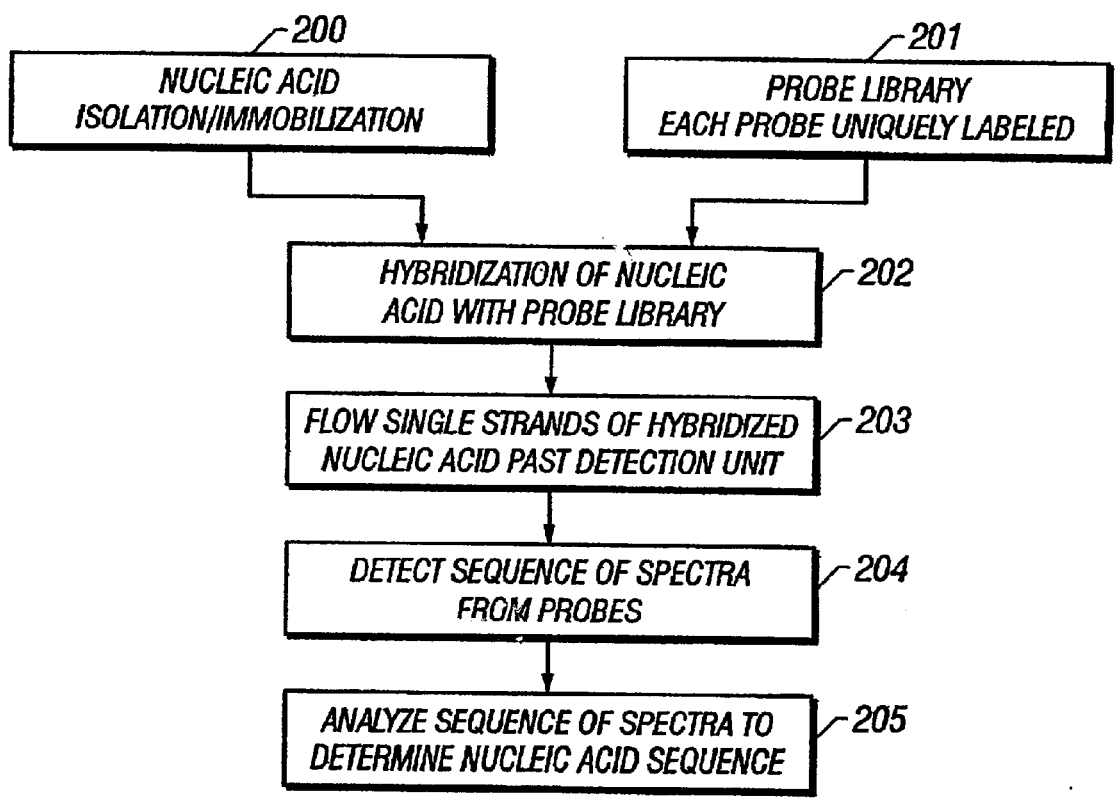
FIG. 4 is a flow chart illustrating an embodied method.

In one embodiment a nucleic acid sequence may be determined by using a decoding method, as illustrated in FIG. 4. The method may entail the immobilization of a single stranded DNA 200, or a double stranded DNA 200 followed by denaturation to a single-stranded molecule. A probe library or libraries may be created 201 such that each probe of the library has an associated label that specifically and uniquely identifies the probe. The nucleic acid is incubated with a probe library or libraries to allow hybridization of the probes to the target sequence 202. The hybridized nucleic acids are manipulated through a micro-fluidic channel where they flow past an excitation source and a detector 203. Emission spectra of the labeled probes may be detected and relayed to a data processing system 204. The sequence of the nucleic acid is determined by comparing the emission spectra and the order in which the emission spectra were detected to a database of spectra for labels associated with each probe 205. The linear sequence of probes hybridized to the nucleic acid can be determined by either statistical calculations or the determination of probe order from a single nucleic acid molecule. In alternate embodiments of the invention individual probes hybridized to the nucleic acid may be ligated to adjacent probes. Ligation of probes would produce a more stable association between probe and target.

The length of nucleic acid analyzed by this method should only be limited by the length of nucleic acid that can be manipulated with out shearing, breaking or other means of degradation, allowing for extended read lengths and faster, more economical sequencing of nucleic acids.

In certain embodiments one or more hybridized nucleic acid molecules may be analyzed sequentially, concurrently or in parallel. In one embodiment hybridized nucleic acids may pass by the detection unit sequentially, that is, one nucleic acid at a time. In another embodiment a plurality of nucleic acids may pass by a detection unit concurrently. In still other embodiments hybridized nucleic acid may be analyzed sequentially or concurrently in parallel processing using an array of microfluidic devices fabricated on a single surface. The data obtained can be converted into a nucleic acid sequence by statistical analysis and processing of the signals detected by a data processing system.

Following detection and analysis by the described methods, one may compare the nucleic acid sequence determined for a given sample or patient with a statistically significant reference group of organisms or normal patients and patients exhibiting a disease. In this way, it is possible to correlate characteristics of the nucleic acid sequences with various organisms or clinical states. Typically, mapping or linkage studies are performed, in some cases in a family of related individuals exhibiting a high occurrence of a disease state or condition, in order to identify a portion of a chromosome associated with the state or condition. That portion of chromosomal DNA may be targeted for analysis by sequencing, for example by isolating or specifically amplifying that region of chromosomal DNA.

Nucleic Acids

Nucleic acid molecules to be sequenced may be prepared by any standard technique. In one embodiment, the nucleic acids may be naturally occurring DNA or RNA molecules. Where RNA is used, it may be desired to convert the RNA to a complementary cDNA. Virtually any naturally occurring nucleic acid may be prepared and sequenced by the methods of the present invention including, without limit, chromosomal, mitochondrial or chloroplast DNA or messenger, heterogeneous nuclear, ribosomal or transfer RNA. Methods for preparing and isolating various forms of cellular nucleic acids are known (See, e.g., *Guide to Molecular Cloning Techniques*, eds. Berger and Kimmel, Academic Press, New York, N.Y., 1987; *Molecular Cloning: A Laboratory Manual*, 2nd Ed., eds. Sambrook, Fritsch and Maniatis, Cold Spring Harbor Press, Cold Spring Harbor, N.Y., 1989). Non-naturally occurring nucleic acids may also be sequenced using the disclosed methods and compositions. For example, nucleic acids prepared by standard amplification techniques, such as polymerase chain reaction (PCRTM) amplification, could be sequenced within the scope of the present invention. Methods of nucleic acid amplification are well known in the art.

Nucleic acids may be isolated from a wide variety of sources including, but not limited to, viruses, bacteria, eukaryotes, mammals, and humans, plasmids, M13, lambda phage, P1 artificial chromosomes (PACs), bacterial artificial chromosomes (BACs), yeast artificial chromosomes (YACs) and other cloning vectors.

Methods of Nucleic Acid Immobilization

In various embodiments, nucleic acid molecules may be immobilized by attachment to a solid surface. Immobilization of nucleic acid molecules may be achieved by a variety of methods involving either non-covalent or covalent attachment to a support or surface. In an exemplary embodiment, immobilization may be achieved by coating a solid surface with streptavidin or avidin and binding of a biotinylated polynucleotide. Immobilization may also occur by coating a polystyrene, glass or other solid surface with poly-L-Lys or poly L-Lys, Phe, followed by covalent attachment of either amino- or sulfhydryl-modified nucleic acids using bifunctional crosslinking reagents. Amine residues may be introduced onto a surface through the use of aminosilane.

Immobilization may take place by direct covalent attachment of 5'-phosphorylated nucleic acids to chemically modified polystyrene surfaces. The covalent bond between the nucleic acid and the solid surface is formed by condensation with a water-soluble carbodiimide. This method facilitates a predominantly 5'-attachment of the nucleic acids via their 5'-phosphates.

DNA is commonly bound to glass by first silanizing the glass surface, then activating with carbodiimide or glutaraldehyde. Alternative procedures may use reagents such as 3-glycidoxypropyltrimethoxysilane or aminopropyltrimethoxysilane (APTS) with DNA linked via amino linkers incorporated either at the 3' or 5' end of the molecule during DNA synthesis. DNA may be bound directly to membranes using ultraviolet radiation. Other methods of immobilizing nucleic acids are known.

The type of surface to be used for immobilization of the nucleic acid is not limited. In various embodiments, the immobilization surface may be magnetic beads, non-magnetic beads, a planar surface, a pointed surface, or any other conformation of solid surface comprising almost any material, so long as the material will allow hybridization of nucleic acids to probe libraries.

Bifunctional cross-linking reagents may be of use in various embodiments. Exemplary cross-linking reagents include glutaraldehyde, bifunctional oxirane, ethylene glycol diglycidyl ether, and carbodiimides, such as 1-ethyl-3-(3-dimethylaminopropyl) carbodiimide.

In certain embodiments a capture oligonucleotide may be bound to a surface. The capture oligonucleotide will hybridize with a specific nucleic acid sequence of a nucleic acid template. A nucleic acid may be released from a surface by restriction enzyme digestion, endonuclease activity, elevated temperature, reduced salt concentration, or a combination of these and similar methods.

Probe Libraries

The term "probe" refers to an oligonucleotide of defined sequence, such as DNA or RNA, or any analog thereof, such as peptide nucleic acid (PNA), which can be used to identify a specific complementary sequence in a nucleic acid.

In certain embodiments one or more labeled probe libraries may be prepared for hybridization to one or more nucleic acid molecules. For example, a set of probes containing all 4096 or about 2000 non-complementary 6-mers, or all 16,384 or about 8,000 non-complementary 7-mers may be used. If non-complementary subsets of probes are to be used, a plurality of hybridizations and sequence analyses may be carried out and the results of the analyses merged into a single data set by computational methods. For example, if a library comprising only non-complementary 6-mers were used for hybridization and sequence analysis, a second hybridization and analysis using the same nucleic acid molecule hybridized to those probe sequences excluded from the first library would be performed.

In certain embodiments, the probe library contains all possible nucleic acid sequences for a given probe length (e.g., a six-mer library would consist of 4096 probes). In such cases, certain probes will form hybrids with complementary probe sequences. Such probe-probe hybrids, as well as unhybridized probes, may be excluded from the channel leading to the detection unit. Methods for the selection and generation of complete sets or specific subsets of probes of all possible sequences for a given probe length are known. In various embodiments, probes of 2, 3, 4, 5, 6, 7, 8, 9, 10, 11, 12, 13, 14, 15 or more nucleotides in length may be used within the scope of the present invention.

In certain embodiments, the probe libraries may comprise a random nucleic acid sequence in the middle of the probe attached to constant nucleic acid sequences at one or both ends. For example, a subset of 12-mer probes could consist of a complete set of random 8-mer sequences attached to constant 2-mers at each end. These probe libraries can be subdivided according to their constant portions and hybridized separately to a nucleic acid, followed by analysis using the combined data of each different probe library to determine the nucleic acid sequence. The skilled artisan will realize that the number of sublibraries required is a function of the number of constant bases that are attached to the random sequences. An alternative embodiment may use multiple hybridizations and analyses with a single probe library containing a specific constant portion attached to random probe sequences. For any given site on a nucleic acid, it is possible that multiple probes of different, but overlapping sequence could bind to that site in a slightly offset manner. Thus, using multiple hybridizations and analyses with a single library, a complete sequence of the nucleic acid could be obtained by compiling the overlapping, offset probe sequences.

Each probe may have at least one covalently attached label or tag. In certain embodiments the probes may have a plurality of attached labels or tags, the combination of which is unique to a particular probe. Combinations of labels can be used to expand the number of unique labels available for specifically identifying a probe in a library. In other embodiments the probes may each have a single unique label attached. The only requirement is that the signal detected from each probe must be capable of uniquely identifying the sequence of that probe.

Oligonucleotide Libraries

In certain embodiments the probe library is an oligonucleotide probe library. Oligonucleotide probes may be prepared by standard methods, such as by synthesis on an Applied Biosystems 381A DNA synthesizer (Foster City, Calif.) or similar instruments. Alternatively, probes can be purchased from a variety of vendors. In embodiments where probes are chemically synthesized, the nanotube label may be covalently attached to one or more of the nucleotide precursors used for synthesis. Alternatively, the label may be attached after the probe has been synthesized.

Peptide Nucleic Acid (PNA) Libraries

In alternative embodiments peptide nucleic acids (PNAs) may be used as probes. PNAs are a polyamide type of DNA analog with monomeric units for adenine, guanine, thymine, and cytosine. PNAs are available commercially from companies such as Perceptive Biosystems. Alternatively, PNA synthesis may be performed with 9-fluoroenylmethoxycarbonyl (Fmoc) monomer activation and coupling using O-(7-azabenzotriazol-1-yl)-1,1,3,3-tetramethyluronium hexafluorophosphate (HATU) in the presence of a tertiary amine, N,N-diisopropylethylamine (DIEA). PNAs can be purified by reverse phase high performance liquid chromatography (RP-HPLC) and verified by matrix assisted laser desorption ionization—time of flight (MALDI-TOF) mass spectrometry analysis.

Labeling of Probes

In certain embodiments a label may be incorporated into a precursor prior to the synthesis of a probe. Internal amino-modifications for labeling at adenine (A) and guanine (G) positions are contemplated. Typically, when internal labeling is required, it is performed at a thymine (T) position using a commercially available phosphoramidite. In certain embodiments library segments with a propylamine linker at the A and G positions are used to internally label a probe. The introduction of an internal aminoalkyl tail allows post-synthetic labeling of the probe. Linkers may be purchased from vendors such as Synthetic Genetics, San Diego, Calif. In one embodiment automatic coupling using the appropriate phosphoramidite derivative of the label is also contemplated. These labels are coupled during the synthesis at the 5'-terminus.

Carbon nanotubes may be covalently attached to a probe. The probes may be oligonucleotides, PNAs or analogs thereof. In general, the covalent attachments are made in such a manner as to minimize steric hindrance between a probe and any labels that may be attached to the same probe or adjacent probes, in order to facilitate probe hybridization to a nucleic acid. Linkers may be used that provide a degree of flexibility to the labeled probe. Homo- or heterobifunctional linkers are available from various commercial sources.

The point of attachment to a base will vary with the base. While attachment at any position is possible, it is preferred to attach at positions not involved in hydrogen bonding to the complementary base. Thus, for example, attachment can be to the 5 or 6 positions of pyrimidines such as uridine, cytosine and thymine. For purines such as adenine and guanine, the linkage is preferably via the 8 position.

Hybridization

In preferred embodiments, hybridization of the nucleic acid to the probe library occurs under stringent conditions that only allow hybridization between fully complementary nucleic acid sequences. Low stringency hybridization is generally performed at 0.15 M to 0.9 M NaCl at a temperature range of 20° C. to 50° C. High stringency hybridization is generally performed at 0.02 M to 0.15 M NaCl at a temperature range of 50° C. to 70° C. It is understood that the temperature and/or ionic strength of a desired stringency are determined in part by the length of the probe, the base content of the target sequences, and the presence of formamide, tetrametylammonium chloride or other solvents in the hybridization mixture. The ranges mentioned above are exemplary and the desired stringency for a particular hybridization reaction is often determined empirically by comparison to positive and/or negative controls.

Processing of Hybridized Nucleic Acid

Once a nucleic acid is hybridized to a probe library the hybridized nucleic acid may be processed. In certain embodiments non-hybridizing probes may be separated from a hybridized nucleic acid either before or after introduction into a microfluidic device. The separation of non-hybridized probes may be accomplished by, for example, selective precipitation, size exclusion columns, selective immobilization of a hybridized nucleic acid or any equivalent technique.

A nucleic acid may be immobilized in an input chamber of a microfluidic device by optical trapping, magnetic trapping, attachment to a chamber wall and similar immobilization methods. A nucleic acid may be attached to an input chamber wall and subsequently hybridized to probe libraries. After incubation with an immobilized nucleic acid, non-hybridized probes can be washed out of an input chamber. Once separated from non-hybridized probes, a hybridized nucleic acid can be released from an input chamber and manipulated through a microchannel, microcapillary, or micropore for analysis. Alternatively, a hybridized nucleic acid that has been separated from non-hybridized probes by selective precipitation, size exclusion columns, or the like may be introduced into an input chamber and manipulated through a microchannel, microcapillary, or micropore for analysis.

A hybridized nucleic acid may be further manipulated by microfluidic sorting, fluidic focusing, or combinations thereof. Hydrodynamics on a micron scale can be used to manipulate the flow of nucleic acids into a microchannel, microcapillary, or a micropore and past a detector where the linear order of hybridized probes can be determined. In one embodiment of the invention microfluidics is used to sort hybridized nucleic acid(s). Microfluidic sorting of hybridized nucleic acids may include filtering of a solution containing hybridized nucleic acids across a comb to separate individual molecules which are subsequently moved into a microchannel, microcapillary, or a micropore one or more molecule at a time.

In another embodiment microfluidics is used to fluidically focus hybridized nucleic acid(s). Fluidic focusing of hybridized nucleic acids may include moving a fluid containing hybridized nucleic acids through a narrowing path at an appropriate velocity to produce a focused stream of fluid flow, thus separating individual molecules and moving the molecules into a microchannel, microcapillary, or a micropore one or more molecule at a time. Manipulation of the fluid flow may be done by using electric, thermal, pressure or vacuum motive forces.

Microfluidic Systems

In certain embodiments, the apparatus described herein may comprise microfluidic devices for separation and manipulation of nucleic acid templates or hybridized nucleic acids. The microfluidic devices may comprise microcapillaries or microchannels capable of moving labeled, hybridized nucleic acids linearly past a detector. A microfluidic device typically contains a solid or semi-solid substrate that is usually planar, i.e., substantially flat or having at least one flat surface. The planar substrates may be manufactured using solid substrates common in the fields of microfabrication, e.g., glass, quartz, silicon, polysilicon and/or gallium arsenide. Common microfabrication techniques, such as photolithographic techniques, wet chemical etching, laser ablation, micromachining, drilling, milling and the like, may be applied in the fabrication of microfluidic devices. Alternatively, polymeric substrate materials may be used to fabricate such devices, including, e.g., polydimethylsiloxanes (PDMS), polymethylmethacrylate (PMMA), polyurethane, polyvinylchloride (PVC), polystyrene polysulfone, polycarbonate, polymethylpentene, polypropylene, polyethylene, polyvinylidine fluoride, ABS (acrylonitrile-butadiene-styrene copolymer), and the like. In the case of such polymeric materials, injection molding or embossing methods may be used to form planar substrates having the channel and reservoir geometries described herein.

The channels and chambers of a microfluidic device may be fabricated into one surface of a planar substrate as grooves, wells or depressions in that surface. A second planar substrate prepared from the same or similar material is overlaid and bonded to the first, thereby defining and sealing the channels and/or chambers of the device. Together, the upper surface of the first substrate, and the lower mated surface of the upper substrate define the channels and chambers of the device.

Movement of fluids through the device may be regulated by computer-controlled pressure and/or electrokinetic forces precisely control the flow of fluids in microfluidic channels. In certain embodiments, electricity is used to drive samples through the channels. In embodiments involving electro-osmosis, computer-driven power supplies located in reservoirs at each end of a channel are activated to generate electrical current through the channel. The current forces molecules with different charge densities to travel through the channels at different rates. A typical speed is one millimeter per second. In embodiments involving electrophoresis, an electric field influences the movement of charged molecules in microfluids moving through the channels.

Alternate methods for moving microfluids include temperature gradients or micropressure. For example, small amounts of pressure applied to microfluids traveling through channels create predictable and reproducible flows. Temperature gradients can move tiny volumes of liquids around nano-sized channels in silicon wafers. Because the surface tension of the microfluids varies with temperature, a temperature gradient of three or four degrees is enough to cause a microfluid to move towards a cold region in its pathway. Chemical modifications to the substrate applied by lithography may amplify the effect by creating a series of chemical levees along the channels.

Optical Trapping Systems

In alternative embodiments an optical trap can be used to manipulate a nucleic acids. An optical trap is a device in which a particle can be trapped near the focus of a strongly focused light beam, such as a laser beam. The particle is held in the trap by an axial gradient force that is proportional to the gradient of the light intensity and points in the direction of increased intensity. In general, single-beam optical trapping can be achieved for particles having sizes ranging from about 10 $\mu$m to about 10 nm. Commercial optical trapping systems are available, such as, LaserTweezers™ 2000 (Cell Robotics, Inc.), Compact Photonic Tweezers (S+L Gmb) and PALM™ Laser-Microscope System (P.A.L.M. GmbH).

In certain embodiments a nucleic acid may be immobilized onto a bead. The bead can then be optically trapped within a hybridization chamber of a microfluidic device. Alternatively, a nucleic acid may be immobilized onto a magnetic bead that is subsequently trapped magnetically.

Detection Unit

In particular embodiments a detection unit may comprise an excitation source and a detector. An excitation source can promote alterations in a label that can result in a signal emission. For example, an electron beam may excite electrons of a carbon nanotube label by coulombic induction, which may result in a fluorescent emission as an excited nanotube returns to its ground state. Emitted energy can be detected by a variety of detectors including, but not limited to microspectrophotometers, photomultiplier tubes, photodiodes with a spectrometer, Fourier-transform spectrophotometers, high precision interferometers and avalanche detectors. In a non-limiting example, the detector may comprise a Jobin-Yvon HRD1 double grating monochromator and GaAs cathode photo-multiplier tube coupled to a computer through a photon counter. For embodiments involving nanotube emission in the visible light range, any high quality spectrophotometer may be used. In certain embodiments, the detector may be integrated onto a chip. In a particular embodiment a micro electron beam may be used as an excitation source. The energy absorbed is emitted as a detectable signal and each label has a unique spectral profile. The skilled artisan will realize that the strength of the emission signal may vary as a function of the orientation of the nanotubes relative to the detector and that detector alignment may be adjusted to maximize the strength of the emitted signal. Alternatively, an array of detectors may be positioned to detect emitted signals irrespective of nanotube orientation.

Excitation Source

In certain embodiments the excitation source may be an electron beam. In alternate embodiments the excitation source may generate other forms of electromagnetic radiation such as UV, visible or infrared light. The method of exciting the carbon nanotube labels is not limited to the disclosed embodiments and any other method of exciting carbon nanotubes known in the art is contemplated. For example, excitation could occur using a UV laser or the 406.7 nm line of a Coherent C100 Krypton ion laser or the 325 nm line of a HeCd laser. In certain embodiments, labeled probes hybridized to a nucleic acid may be excited and detected while bound to the nucleic acid, during transit past a detector. In alternate embodiments, probes may be released after transit through a microchannel, microcapillary, or micropore by enzymatic degradation of a nucleic acid or disruption of binding, for example, by heating. Released probes may be further manipulated by flow through an extended microfluidic device to an appropriate detector before identification.

Figure 5:
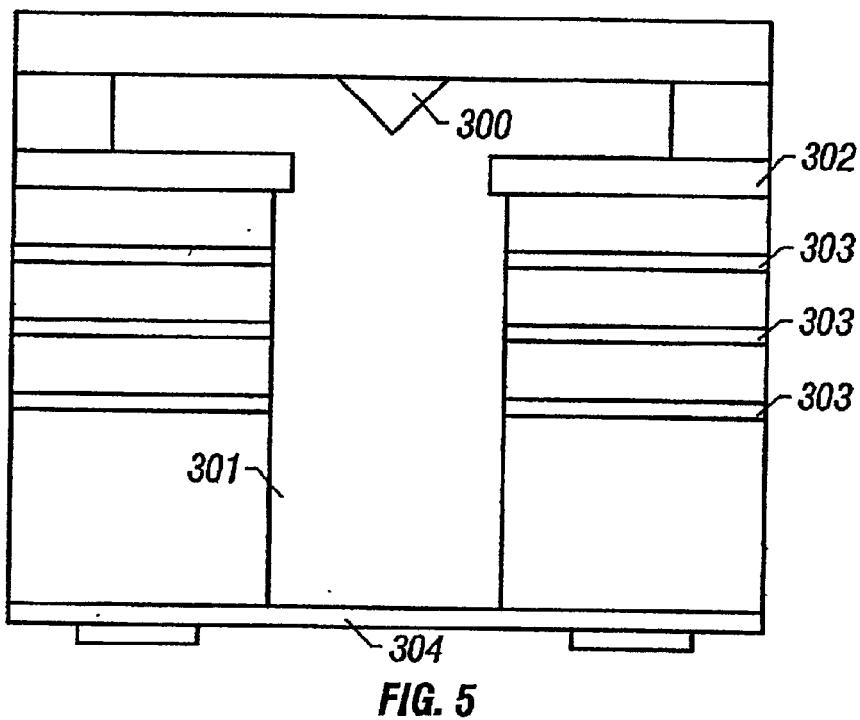
FIG. 5 illustrates one embodiment of a micro column electron beam source.

In certain embodiments the excitation source may be a micro column electron beam (micro e-beam) source as illustrated in FIG. 5. The excitation source illustrated in FIG. 5 may be made by using microfabrication techniques known in the art and is based largely on the micromachining of silicon. The stacked parts of the device may be assembled in a vacuum using a wafer-to-wafer bonding approach. An electron source 300 is positioned at the opening of an evacuated column 301. The opening of the evacuated column 301 has an associated low-voltage gate electrode 302. Perpendicular to the evacuated column's long axis are aligned high-voltage acceleration, deflection, and focusing electrodes 303. The evacuated column is typically sealed at the far end by an electron transparent membrane 304 that is typically operatively coupled to a microchannel. An electron transparent membrane 304 is positioned so that an electron beam can be focused onto a channel. The channel provides a microfluidic path for the passage of nucleic acids hybridized to labeled probes. The e-beam can be directed so it is incident with passing nucleic acid(s) and excites an associated labeled probe. The excited label will emit spectra characteristic of the probe. Emitted photons may detected by a detector array and may be stored in a processing unit for further analysis.

Figure 6:
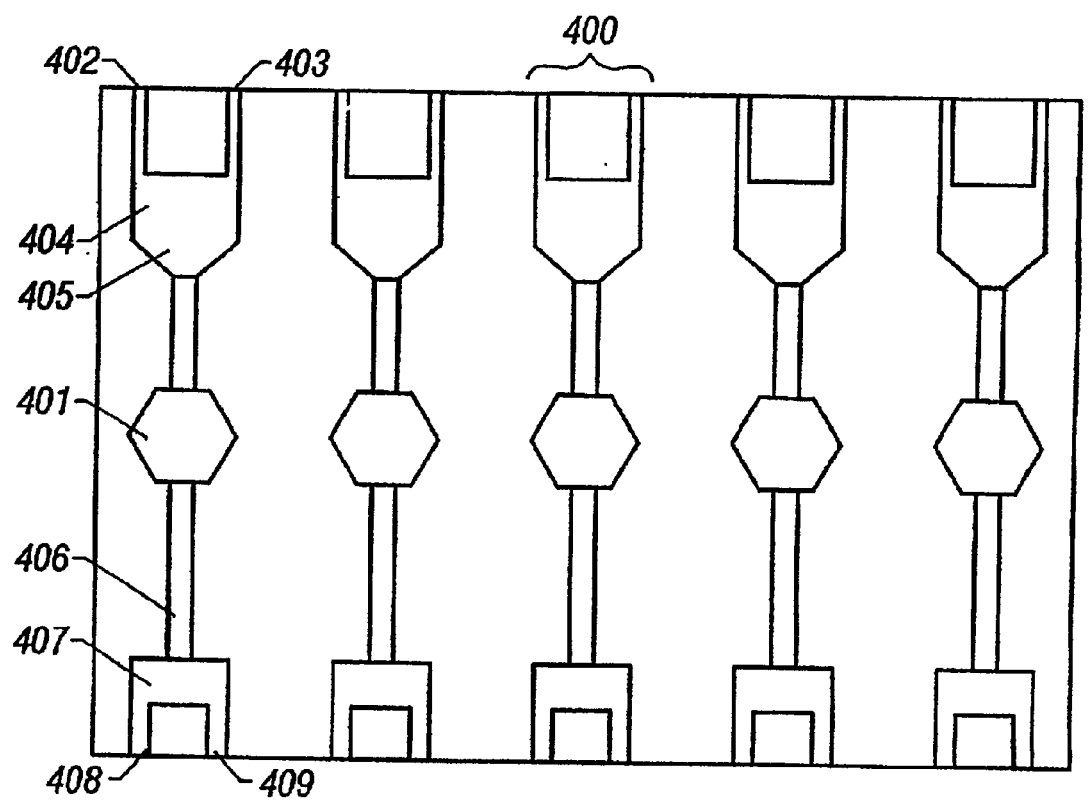
FIG. 6 illustrates one embodiment of an array of microfluidic sequencing units.

In one embodiment an array of micro column electron beam sources may be fabricated onto a support. FIG. 6 shows a sequencing apparatus 400 comprising an array of microfluidic electron induced fluorescence detectors. Each of the microfluidic devices comprises a micro column electron beam source 401, an inlet port 402, an outlet port 403, an input chamber 404, fluidic focusing region 405, microchannel 406, an output chamber 407, inlet exit port 408 and an outlet exit port 409. The input chamber 404 is in fluid communication with the output chamber 407 via the microchannel 406. A single hybridization mixture can be introduced to and analyzed in each device 400 of the array. Alternatively, distinct hybridization mixtures can be introduced to and analyzed in separate devices 400 of the array.

Information Processing and Control System and Data Analysis

In certain embodiments, the sequencing apparatus may be interfaced with an information processing and control system. In an exemplary embodiment, the system incorporates a computer comprising a bus or other communication means for communicating information, and a processor or other processing means coupled with the bus for processing information. In one embodiment, the processor is selected from the Pentium® family of processors, including the Pentium® II family, the Pentium® III family and the Pentium® 4 family of processors available from Intel Corp. (Santa Clara, Calif.). In alternative embodiments, the processor may be a Celeron®, an Itanium®, or a Pentium Xeon® processor (Intel Corp., Santa Clara, Calif.). In various other embodiments, the processor may be based on Intel® architecture, such as Intel® IA-32 or Intel® IA-64 architecture. Alternatively, other processors may be used.

The computer may further comprise a random access memory (RAM) or other dynamic storage device (main memory), coupled to the bus for storing information and instructions to be executed by the processor. Main memory may also be used for storing temporary variables or other intermediate information during execution of instructions by processor. The computer may also comprise a read only memory (ROM) and/or other static storage device coupled to the bus for storing static information and instructions for the processor. Other standard computer components, such as a display device, keyboard, mouse, modem, network card, or other components known in the art may be incorporated into the information processing and control system. The skilled artisan will appreciate that a differently equipped information processing and control system than the examples described herein may be desirable for certain implementations. Therefore, the configuration of the system may vary within the scope of the present invention.

In particular embodiments, the detection unit may also be coupled to the bus. Data from the detection unit may be processed by the processor and the processed and/or raw data stored in the main memory. Data on known emission spectra for labeled probes may also be stored in main memory or in ROM. The processor may compare the emission spectra from probes in the channel to the stored spectra to identify the sequence of probes passing along the channel. The processor may analyze the data from the detection unit to determine the sequence of the nucleic acid.

The information processing and control system may further provide automated control of the sequencing apparatus. Instructions from the processor may be transmitted through the bus to various output devices, for example to control the pumps, electrophoretic or electro-osmotic leads and other components of the apparatus.

It should be noted that, while the processes described herein may be performed under the control of a programmed processor, in alternative embodiments, the processes may be fully or partially implemented by any programmable or hardcoded logic, such as Field Programmable Gate Arrays (FPGAs), TTL logic, or Application Specific Integrated Circuits (ASICs), for example. Additionally, the method of the present invention may be performed by any combination of programmed general purpose computer components and/or custom hardware components.

In certain embodiments, custom designed software packages may be used to analyze the data obtained from the detection unit. In alternative embodiments, data analysis may be performed using an information processing and control system and publicly available software packages. Non-limiting examples of available software for DNA sequence analysis includes the PRISM™ DNA Sequencing Analysis Software (Applied Biosystems, Foster City, Calif.), the Sequencher™ package (Gene Codes, Ann Arbor, and a variety of software packages available through the National Biotechnology Information Facility.

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Probe Library

Oligonucleotides are either purchased from vendors such as Genetic Designs, Inc. Houston, Tex. or made on an Applied Biosystems 381A DNA synthesizer. The probe library is synthesized using nucleotide or nucleotide analogs that have been covalently modified with carbon nanotubes, with each probe incorporating a unique nanotube label.

Hybridizations are obtained with probes six to eight nucleotides in length. These procedures allow maximal reduction in the number of probes per library, reducing the costs of sequencing reaction. A complete library of 4,096 random hexamers, each labeled with a unique combination of one or more nanotube labels is synthesized as described above. Nanotubes are covalently attached to a nucleotide precursor prior to probe synthesis.

Example 2

Hybridization Procedures

DNA to be sequenced is immobilized by optical trapping in an input chamber of a microfluidic device. The input chamber is filled with a hybridization solution (0.5 M Na2 HPO4, pH 7.2, 7% sodium lauroyl sarcosine). A hexamer probe library as described above is added and allowed to hybridize to the nucleic acid by incubation at 60° C. for 1 hr. Probe concentration is 10 $\mu$g of labeled DNA in 100 $\mu$l of hybridization solution. Hybridization is stopped by the introduction of 6×SSC washing solution and non-hybridized probes are removed by washing multiple times. The nucleic acid is released from the optical trap and enters the channel for detection of hybridized probes.

Example 3

Analysis of Bound Probes

The hybridized nucleic acid is released from the chamber and an electro-osmotic motive force is applied, driving the hybridized nucleic acid down the channel past the detection unit. As each probe passes the microelectron beam and microspectrophotometer the fluorescence of the associated nanotube label is detected as a spectral profile, which is associated with a particular probe of known sequence. The linear order of probe molecules is assembled by the analysis of multiple hybridizations. Once the linear order of probes is obtained the nucleic acid sequence is determined.

All of the COMPOSITIONS, METHODS and APPARATUS disclosed and claimed herein can be made and executed without undue experimentation in light of the present disclosure. While the compositions and methods of this invention have been described in terms of preferred embodiments, it will be apparent to those of skill in the art that variations may be applied to the COMPOSITIONS, METHODS and APPARATUS and in the steps or in the sequence of steps of the methods described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A method of identifying one or more nucleic acids comprising:

a) obtaining a probe for each nucleic acid to be identified;
   b) attaching at least one carbon nanotube to each probe;
   c) hybridizing the probes to the nucleic acids;
   d) exciting the nanotubes; and
   e) detecting the emission spectra of the excited nanotubes wherein the emission spectra are correlated with the probes hybridized to one or more nucleic acids.

2. The method of claim 1, wherein the nanotubes are excited with an ultraviolet (UV) laser or an electron beam.

3. The method of claim 2, further comprising identifying one or more peaks in the optical emission spectrum of each nanotube.

4. The method of claim 3, further comprising determining the wavelength of each peak.

5. The method of claim 1, wherein at least one probe is attached to at least two nanotubes.

6. The method of claim 1, wherein the nanotubes are single wall carbon nanotubes.

7. The method of claim 1, wherein nanotubes attached to different probes exhibit distinguishable emission spectra.

8. The method of claim 1, wherein the probes are oligonucleotides, chemically modified oligonucleotides, oligonucleotide analogs or peptide nucleic acids.

9. The method of claim 8, wherein the probes comprise all possible nucleotide sequences for a probe of defined length.

10. The method of claim 9, wherein the probe length is selected from the group consisting of 4, 5, 6, 7 and 8 nucleotides.

11. The method of claim 8, wherein at least one probe is attached to at least two nanotubes.

12. The method of claim 8, wherein the probes comprise random nucleotide sequences.

13. The method of claim 8, wherein the probes comprise at least one constant nucleotide.

14. The method of claim 8, wherein the probe length is selected from the group consisting of 4, 5, 6,7, 8, 9, 10, 11, 12, 13, 14 and 15 nucleotides.

15. The method of claim 8, wherein the probe length is greater than 15 nucleotides.

16. The method of claim 1, further comprising identifying the probes that hybridize with the nucleic acid.

17. The method of claim 1, wherein the nucleic acids are attached to a substrate.

18. The method of claim 17, wherein the substrate is a chip.

19. The method of claim 16, further comprising identifying the sequence of probes that are hybridized with the nucleic acid.

20. The method of claim 19, further comprising moving the hybridized nucleic acid past a detector, wherein the hybridized probes move past the detector in a linear sequence.

21. The method of claim 20, wherein the hybridized nucleic acid moves past the detector in a microchannel or microcapillary.

22. The method of claim 19, further comprising separating unhybridized probes from probes hybridized to the nucleic acid.

\* \* \* \* \*

UNITED STATES PATENT AND TRADEMARK OFFICE
CERTIFICATE OF CORRECTION

PATENT NO. : 6,821,730 B2
DATED : November 23, 2004
INVENTOR(S) : Hannah

It is certified that error appears in the above-identified patent and that said Letters Patent is hereby corrected as shown below:

Column 6,
Line 9, before "1400", insert -- or --.

Column 10,
Line 1, delete "(PCRTM)" and insert -- (PCR$^{TM}$) --.

Column 17,
Line 14, after "Arbor", insert -- MI), --.

Signed and Sealed this

Twenty-fourth Day of May, 2005

JON W. DUDAS
*Director of the United States Patent and Trademark Office*